US007947303B2

(12) United States Patent
Kessler et al.

(10) Patent No.: US 7,947,303 B2
(45) Date of Patent: May 24, 2011

(54) SUPPLEMENT TO BE ENTERALLY ADMINISTERED FOR PARENTERAL NUTRITION OR PARTIAL ENTERAL/ORAL NUTRITION OF THE CRITICALLY ILL, THE CHRONICALLY ILL AND PEOPLE WITH MALNUTRITION

(75) Inventors: Barbara Kessler, Kronberg (DE); Angelika Riedel, Gravenwiesbach (DE); Ulrich Suchner, Erding (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 1346 days.

(21) Appl. No.: 10/432,915

(22) PCT Filed: Nov. 14, 2001

(86) PCT No.: PCT/EP01/13163

§ 371 (c)(1), (2), (4) Date: Nov. 20, 2003

(87) PCT Pub. No.: WO02/39978

PCT Pub. Date: May 23, 2002

(65) Prior Publication Data

US 2004/0097404 A1 May 20, 2004

(30) Foreign Application Priority Data

Nov. 17, 2000 (DE) .................................. 100 57 290

(51) Int. Cl.

| | |
|---|---|
| ***A01N 37/00*** | (2006.01) |
| ***A01N 61/00*** | (2006.01) |
| ***A61K 38/00*** | (2006.01) |
| ***A61K 47/00*** | (2006.01) |
| ***A23J 1/00*** | (2006.01) |
| ***A23L 1/30*** | (2006.01) |
| ***A23L 3/015*** | (2006.01) |
| ***C12P 13/14*** | (2006.01) |
| ***C07C 229/00*** | (2006.01) |

(52) U.S. Cl. ........ 424/439; 426/648; 426/656; 426/665; 435/110; 514/1.1; 514/557; 562/563

(58) Field of Classification Search ........................ None
See application file for complete search history.

(56) References Cited

U.S. PATENT DOCUMENTS

| | | | | |
|---|---|---|---|---|
| 3,698,912 | A * | 10/1972 | Winitz | 426/656 |
| 5,066,500 | A * | 11/1991 | Gil et al. | 426/72 |
| 5,326,569 | A * | 7/1994 | Acosta et al. | 424/440 |
| 5,569,680 | A | 10/1996 | Wu | |
| 6,277,432 | B1 * | 8/2001 | Chang | 426/602 |
| 6,369,252 | B1 * | 4/2002 | Akoh | 554/227 |
| 7,115,297 | B2 * | 10/2006 | Stillman | 426/590 |

FOREIGN PATENT DOCUMENTS

| | | | |
|---|---|---|---|
| EP | 0 547 099 | B1 | 6/1993 |
| EP | 0 705 542 | A1 | 4/1996 |
| EP | 0 756 827 | A2 | 2/1997 |
| EP | 0 891 719 | A1 | 1/1999 |
| WO | WO-94/14458 | | 7/1994 |
| WO | WO-99/01044 | | 1/1999 |

OTHER PUBLICATIONS

English language abstract of EP 0 756 827 A2 (Feb. 5, 1997).
A. Wachtershauser, J. Stein, Rationale for the Luminal Provision of Butyrate in Intestinal Diseases, Eur. J. Nutr. 39, pp. 164-171 (2000).
Abstract of "Current Opinion in Clinical Nutrion and Metabolic Care," Medline (2001367014); pp. 339-344 (Sep. 2000).
Abstract of "Critical Care Medicine," Elsevier Sc. B.V.; pp. 159-164 (1990).
U. Suchner, U. Senftleben, T. W. Felbinger; "Immunfunktion und Organversagen," Anaesthesist; pp. 460-465 (2000).

* cited by examiner

*Primary Examiner* — Debbie K Ware
(74) *Attorney, Agent, or Firm* — Occhiuti Rohlicek & Tsao LLP

(57) ABSTRACT

A supplement to be administered enterally to maintain or restore the intestinal intestinal barrier of the critically or chronically ill and people with malnutrition is described.
This contains as solution, in each case based on a daily dose,
a) glutamine and/or glutamine precursors in an amount in the range from 15 to 70 g,
b) at least two representatives from the group of substances having antioxidant activity, and
c) short-chain fatty acids and/or precursors of short-chain fatty acids in an amount of from 0.5 to 10 g.

33 Claims, No Drawings

SUPPLEMENT TO BE ENTERALLY ADMINISTERED FOR PARENTERAL NUTRITION OR PARTIAL ENTERAL/ORAL NUTRITION OF THE CRITICALLY ILL, THE CHRONICALLY ILL AND PEOPLE WITH MALNUTRITION

The present invention relates to a supplementary food (referred to hereinafter as supplement) which is to be administered or can be administered enterally for the critically ill (intensive care patients or surgical patients), the chronically ill or people with malnutrition in addition to a parenteral or inadequate oral nutrition, with which the intention is for severe disruptions of the intestinal barrier either to be prevented in the form of protection or to be treated after they have occurred.

The intestinal barrier includes for the purposes of the invention not only the epithelial layers of the intestinal mucosa but also the microflora, the peristalsis, the mucus production and the regional immune defenses as constituent of gut-associated lymphoid tissue (GALT). The intestinal barrier thus represents the first line of defense against a threatening invasion by pathogenic microbes and toxins—called translocation hereinafter. The importance of "care" thereof has already been indicated in connection with early enteral nutrition therapy of the critically ill.

Life-threatening disruptions of other organ functions, such as, in particular, of heart, lung and kidneys, can now be substantially compensated by organ replacement or other therapeutic interventions. This does not apply to the intestine. The "intestine" with its vital barrier functions has consequently in many cases become the most critical organ for the prognosis of the abovementioned groups of patients.

Patients regarded as critically ill or very seriously ill for the purposes of the invention are those having pathological conditions like those occurring, for example in association with serious infections and traumas, polytraumas, acute radiation injury, severe burns, but also major operations, which conditions are associated with disruptions of vital functions such as, for example, of the breathing, of circulatory stability or of excretory functions. Patients regarded as chronically ill for the purposes of the invention are those having benign or malignant chronically wasting pathological conditions which proceed without threatening the vital functions. These patients are often capable of only inadequate intake of a conventional enteral/oral nutrition because of defective digestion and assimilation such as, for example, associated with chronically inflammatory bowel disorders with suppressed immune system (Crohn's disease or ulcerative colitis) or, for example, tumor patients. Patients with malnutrition for the purposes of the invention are regarded as being those incapable for a wide variety of reasons of an adequate intake of food, such as, for example, malnourished geriatric patients.

Great advances have been achieved in the initial management of severely traumatized patients. This is impressively documented by a decrease in the early mortality of these patients. The late mortality of severely traumatized, critically ill patients is, however, still burdened by a high incidence of sepsis and multiorgan failure (MOF). Collapse of the intestinal intestinal barrier of the gastrointestinal tract has been recognized as the essential entry point for pathogens and toxins. "Translocation" of live bacteria and of toxins through the intestinal wall into the portal circulation is followed by uptake thereof also into other organs such as the liver and the lung. Especially the Kupfer cells of the reticuloendothelial system of the liver, and the alveolar macrophages of the lung, are involved in mediating the stress response which then develops. They are known to be the sites of the production of proinflammatory mediators such as, for example, the interleukins Il-1, Il-2, tumor necrosis factor TNF-$\alpha$ and prostaglandin $E_2$. These mediators are the cause and modulators of the clinically imposing generalized inflammatory reaction, which is referred to hereinafter as systemic inflammatory response syndrome (SIRS). Greatly simplified, the ideas about the systemic inflammation of visceral origin are summarized by the principle of "the intestine as the starter" and "the liver as the engine" of multiorgan failure.

According to recent findings, nutritional therapeutic factors such as, for example, states of malnutrition or a lack of enteral nutrition act to promote the development of bacterial translocation phenomena. This applies in particular to the critically ill who, owing to current intestinal hypoperfusion and subsequent formation of free radicals during reperfusion, are exposed to a high risk of disruption of the intestinal intestinal barrier. It is becoming increasingly clear that enteral nutrition procedures may make an important contribution to maintaining the structure and function of the intestinal mucosa. In addition, there is unambiguous evidence that the risks of bacterial translocation, and the systemic infections arising therefrom, can be minimized through enteral supply of substrates. The possible advantages of early enteral nutrition of the critically ill can be summarized at present by 4 points:

1. Early enteral nutrition of the critically ill contributes to protection of the intestinal barrier to regeneration thereof after previous mucosal trauma associated with (for example visceral hypoperfusion) and reduces the incidence of infections and of organ dysfunctions based on a reduced intestinal translocation event.
2. Minimal enteral nutritions started within hours post-trauma leads to a reduced release of stress hormones and mediators and thus to a reduced stress response, which has the subsequent effects of lower energy consumption and reduced catabolism of the patient.
3. The choice of the more physiologically enteral route of administration, which includes the visceral first pass effect, results in an improvement in substrate utilization and
4. an increase in substrate tolerability. The increase in substrate utilization is manifested not only by a more favorable substrate homeostasis and an improvement in visceral protein synthesis but eventually in an optimization of the nutritional status. The improvement in substrate tolerability is manifested clinically by a lower rate of side effects. This relates in particular to the visceral organs such as pancreas, liver, intestine and is evident in a smaller rise in the integrity parameters and in better maintenance of intestinal absorption capacity. In addition, a reduction in the incidence of gastrointestinal hemorrhages has repeatedly been observed.

According to the current view, therefore, nutrition of the critically ill must not aim at complete by-passing of the intestinal tract as long as the intestine can still undertake its functions at least in part. This can also be extended to chronically ill patients—especially those with inflammatory bowel disorders.

However, the critically ill, as well as chronically ill patients with inflammatory bowel disorders, frequently show only inadequate gastrointestinal tolerance of large volumes of conventional enteral nutrient solutions. This applies especially to the requirement-covering amounts of calorie and nitrogen suppliers (glucose, fat, amino acids). The volumes necessary for enteral requirement-covering administration of conventional nutrient solutions are typically 1.5-2 liters for a daily dose (tube feeding) and are scarcely tolerated by these patients even if the nutrient solution is administered by the jejunal route of administration. Gastric administration is frequently particularly difficult because of disturbances of gastric emptying.

In addition, both the critically and the chronically ill are subject to long-lasting, severe metabolic stress, the post-injury syndrome, which is associated with a catabolic metabolic status with an increased resting energy requirement. This leads to an increased requirement for selected macro- and micronutrients such as, for example glutamine or defined vitamins and trace elements. Deficiency thereof is associated with severe impairments of immune and organ functions and causes an increase in morbidity and mortality.

An insufficient supply of defined nutrients to the critically and chronically ill to maintain or restore the intestinal barrier is thus based firstly on the possible enteral intake being inadequate and secondly on the increased requirement for these substrates. In seriously malnourished patients, translocation may likewise occur due to substrate deficits and subsequent disruption of the intestinal intestinal barrier and may also lead in these patients to systemic inflammation which, although it occurs to a slightly less marked extent than in the critically and chronically ill, may equally lead to infectious complications.

Until now, important substrates protecting the intestinal barrier have mainly been supplied by the parenteral route. However, it has not been possible by this route to achieve the desired protective and therapeutic effect on the intestinal barrier.

Substrates which can be administered enterally have already been described. Thus, EP-A-875,155 discloses a perioperative drink which, besides carbohydrates, contains glutamine or a glutamine precursor. WO-A-98/41216 discloses a composition for preventing hepatic steatosis which, besides a completing agent for bile acids, may contain an immunonutrient.

WO-A-92/09277 discloses a composition which can be administered orally or parenterally and which, besides free L-glutamine, contains at least one derivative of L-glutamine and, where appropriate, at least one precursor of L-glutamine.

This invention is based on the object of providing a supplement which is to be administered or can be administered enterally to a critically and chronically ill patient or to a person with malnutrition in addition to partial or complete parenteral nutrition or in addition to inadequate enteral/oral nutrition in order to maintain or restore the intestinal barrier function. A further object is to provide a nutritional system composed of parenteral and enteral nutrition which is adapted to the current stress situation. This is intended in the critically and chronically ill or malnourished patients to counteract the threat of "bowel failure", to decrease the incidence of infections and organ failure conditions, to reduce mortality and to minimize time during which parenteral nutrition is necessary.

These objects are generally achieved by providing a supplement to be administered enterally in addition to a partial or complete parenteral nutrition or in addition to an inadequate enteral/oral nutrition, which supplement is conditioned so that a) the enterally administered substrates with a protective/therapeutic effect on the intestinal intestinal barrier are detached from the substrate supply necessary quantitatively to cover the energy and protein requirements; b) the "luminally" (enterally) necessary supply of protective/therapeutic substrates is ensured; c) the protective/therapeutic dosages are ensured; and d) the protective/therapeutic substrates are given in an "integrated system", i.e. in a defined ratio of amounts, because their optimal effects is linked to the simultaneous appropriate availability of all individual substrates.

These objects are specifically achieved by adding to the supplement which is to be administered enterally and is based on a daily dose in combination a) glutamine and/or glutamine precursor in an amount in the range from 15 to 70 g, b) at least two representatives from the group of the class acting as antioxidants and c) short-chain fatty acids and/or precursors of short-chain fatty acids, in particular tributyrin, in an amount in the range from 0.5 to 10 g together with, where appropriate, further immuno/pharmaconutrients oriented according to the particular pathological condition.

The term glutamine precursor means compounds which contain glutamine which is released by metabolic activities. Examples of glutamine precursors are derivatives of glutamine such as esters, amides, N-alkylated glutamine, salts or keto precursors of glutamine such as α-ketoglutarate, and short-chain glutamine-containing peptides such as di- to decapeptides, preferably tripeptides, and very particularly preferably dipeptides. Examples of tripeptides are X-Gln-X', X-X'-Gln and X-Gln-Gln, where X and X' are naturally occurring amino acids.

Preferred tripeptides are Ala-Gln-Ala, Ala-Ala-Gln, Ala-Gln-Gln Gly-Gln-Gly, Gly-Gly-Gln, Gly-Gln-Gln, Ala-Gln-Gly, Gly-Gln-Ala, Ala-Gly-Gln and Gly-Ala-Gln.

Examples of dipeptides are X-Gln where X represents naturally occurring amino acids. Preferred dipeptides are Ala-Gln and Gly-Gln.

Stated amounts in the tests of glutamine precursors are based on the glutamine content of these precursors.

The term short-chain fatty acids means carboxylic acids having two to five, preferably two to four, carbon atoms. Examples thereof are acetic acid, propionic acid, α-methylpropionic acid, pentanoic acid (valeric acid) and, in particular, butyric acid.

The term precursors of short-chain fatty acids means compounds which contain short-chain fatty acids which are released by metabolic activities. Examples thereof are salts or esters of short-chain fatty acids. The esters may be derived from monohydric or polyhydric alcohols. Examples of esters are methyl or ethyl esters, phospholipids or, in particular glycerol esters. Esters of polyhydric alcohols may, besides short-chain, also contain medium or long-chain fatty acids. In the case of esters of polyhydric alcohols with different fatty acids, all the acid moieties are preferably derived from short-chain fatty acids.

Glycerol esters of short-chain fatty acids are preferred, and tributyrin (=glycerol triester of butyric acid) is particularly preferred. Stated amounts in the case of precursors of short-chain fatty acids are based on the content of short-chain fatty acids in these precursors.

The term immuno/pharmaconutrients means nutrient components which are present in the daily total nutrient supply from enteral, and where appropriate, parenteral administration in higher concentrations than corresponds to the recommended daily dose according to the RDA (recommended dietary allowances). This concept of nutrition with immuno/pharmaconutrients which acts directly on the intestinal mucosa and, via the portal vein, on the liver, in addition to parenteral nutrition or in addition to a partial oral/enteral nutrition, serves to compensate the fall in concentration of substrates, which is caused locally by the stress situation, and an impairment associated therewith or the loss of vital metabolic functions, to assist, or to regulate in an advantageous manner, the immune system and/or certain biochemical/physiological metabolic processes, and to ensure the integrity of the intestinal intestinal barrier.

The term daily dose means the volume of the supplement of the invention which is to be administered for the particular case of use. Typical daily doses may be up to 2000 ml, and are preferably in the range between 200 to 1000 ml, and very particularly preferably 400 to 500 ml.

The supplement of the invention is thus used for all the abovementioned groups of patients for whom nutrition must be ensured parenterally or can be carried out only partly enterally/orally, as an additional food which can be administered or is to be administered enterally. The supplement of the invention now makes it possible to improve crucially the intestinal barrier functions and thus the prognosis of the patients where this is determined by the intestinal barrier functions. The previous practice of early enteral nutrition or enteral minimal nutrition has not been able to make this therapeutic contribution because it was essentially directed at quantitatively reliable supply of energy and protein. The supplement of the invention is the first to provide in the necessary concentrations and ratios of amounts the substrates which are indispensable for maintaining the structure and function of rapidly proliferating tissues such as mucosal cells or immunocompetent cells. It is the high-dose enteral supply of the substrates described hereinafter in the supplement of the invention which have the greatest importance for the maintenance (protection) or the restoration (therapy) of the intestinal barrier.

The enteral supplement is low-energy according to the invention, whereas the parenteral nutrition serves as the main source for the supply of energy and nitrogen suppliers, water and electrolytes, especially at the start of the artificial nutrition of a critically ill patient. The enteral supplement can be administered, dissolved in a suitable solvent, preferably water, either orally or via a tube placed in the gastrointestinal cavity in a daily dose which normally does not exceed 1 liter. The supplement of the invention may, besides dissolved ingredients, also contain dispersed, suspended and/or emulsified ingredients.

It is advantageous to begin at the beginning of the treatment of a critically or chronically ill patient with a supplement volume of 500 ml per daily dose. As the patient's general condition improves stepwise it is then possible to supply energy and nitrogen suppliers to cover the calorie and protein requirements, and water and electrolytes, increasingly via the enteral administration route.

The substrate composition of the invention varies in accordance with the underlying volumes, a distinction being made hereinafter between supplement I (smaller volumes such as 500 ml) and supplement II (larger volumes such as 1000 ml).

Supplement I:

Supplement I of the invention which is to be administered enterally has, besides glutamine and/or glutamine precursor and short-chain fatty acid and/or precursor thereof, such as tributyrin, as essential ingredients also at least two, but preferably more, antioxidants or nutrients having antioxidant activity, which may be for example vitamin C, vitamin E, S-adenosylmethionine, cysteine, cystine, taurine, glutathione, selenium, zinc, polyphenols and carotenoids, preferably β-carotene, which generally serve to maintain the intestinal intestinal barrier and which are used in particular in a synergistic manner to control the free radicals which are produced during oxidative stress.

The enteral supplement of the invention may also advantageously have precursor substances for DNA and RNA synthesis, preferably in the form of nucleotides. The supplement of the invention may additionally also have substrates which are formed under normal conditions from bulking agents by microorganisms and favor the metabolism of the colonocytes, such as, for example, one or more substances having a calcium-antagonistic effect, in particular glycine.

The glutamine-rich supplement with the antioxidants and the short-chain fatty acids and/or precursors thereof, such as tributyrin, to which preferably nucleotides and/or glycine are also added in the concentrations lying within the stated range limit is intended to be administered by the enteral route to people with malnutrition and to the critically or chronically ill at the start of treatment in addition to a complete parenteral nutrition or in addition to an enteral/oral nutrition. It is also possible, in place of the substances mentioned, to employ compounds having the same physiological effect, e.g. α-ketoglutarate for glutamine.

The patient can take the supplement either orally or via a tube. The supplement is preferably dissolved in water and is preferably in daily dose portions and, in this case, is present for example as solution of 500 ml in a bag or a bottle. Portions with a volume of, for example, 250 ml are, however, also possible, in which case the stated amounts based on a daily dose relate to a volume of 500 ml.

Since the energy and nitrogen suppliers necessary for complete nutrition are, where possible, administered parenterally at the start of treatment of a patient who is critically or chronically ill within the meaning of the invention, because they are tolerated scarcely or not at all by the enteral route, the supplement I which is to be administered enterally at the start of treatment must be virtually calorie-free, i.e. should not exceed a total amount of energy of 400 kcal per day. For this reason, the enteral supplement of the invention intended for starting the treatment of a critically or chronically ill patient ought to be fat-free, with the exception of component c), and have as protein ingredients at the most the amino acids glutamine, glycine and, where appropriate, alanine (for example in the dipeptide together with glutamine) and cysteine (as antioxidant) and should not exceed a maximum amount of 20 g of carbohydrates per daily dose (preferably in the form of maltodextrins).

Examples of the range of application of supplement I are:

- parenterally fed patients without contraindication for enteral supply of substrates with, at the same time, a high degree of intolerance to conventional enteral nutrient solutions (e.g. in cases of SIRS, sepsis, high-dose catecholamine therapy, multiorgan failure, burns), major abdominal surgery,
- patients who must be fasted before diagnostic procedures and before surgical interventions, inflammatory bowel disorders (Crohn's disease, ulcerative colitis),
- mucositis, stomatitis (after chemo-, radiotherapy, bone marrow transplantations),
- short bowel syndrome,
- acute pancreatitis.

The invention also relates to the use of the abovementioned components a) to c) for the for the production of a supplement to be administered enterally for the treatment of the abovementioned diseases.

Supplement II:

After the bowel function has evidently stabilized and when larger volumes of supplement I comprising, for example, 500 ml are tolerated, part of the parenteral complete food can then be administered via the enteral supplement II which is adapted to these tasks. In this case, it is possible to add to the enteral supplement in addition to the nutrient already present in the small-volume initial supplement (supplement I), based on a daily dose, up to a maximum of 30 g of protein, in particular in the form of a protein hydrolyzate from whey, and/or up to a maximum of 45 g of fat, in particular in the form of medium chain ($C_6$-$C_{12}$) triglycerides (MCT) and essential fatty acids. The daily dose for the carbohydrates (preferably in the form of maltodextrins) in the larger-volume enteral supplement II for a malnourished person and a critical or chronically ill patient can then be increased, besides possible partial parenteral nutrition, for example up to 115 g.

It is additionally advantageous to add up to a maximum of 1 mg of chromium, for example in the form of chromium trichloride, to the supplement II which is to be administered enterally in addition to the partial parenteral nutrition.

A supplement which has such a composition and is to be administered to a malnourished person or critically or chronically ill patient in addition to possible partial parenteral nutrition or in addition to partial enteral/oral nutrition may normally occupy a volume of up to 1000 ml per daily dose and then comprises up to 1000 kcal. This supplement may then be put in portions with volumes of 1000 ml, 500 ml and 250 ml in a bag or a bottle, where the stated amounts stated for a daily dose are based on a volume of 1000 ml.

Examples of the area of application of supplement II are:

- parenterally fed patients without contraindication for enteral supply of substrates with less pronounced intolerance to conventional enteral nutrient solutions,
- malnourishment in
  - chronic bowel disorders
  - geriatric patients
  - neurological disturbances,
  - mucositis/stomatitis,
  - tumor cachexia,
  - preventive preoperative nutrition.

The invention also relates to the use of the abovementioned components a) to c) for the for the production of a supplement to be administered enterally for the treatment of the abovementioned diseases.

The amounts stated below for the respective defined substrates in the supplement of the invention, based on a daily dose, represent a balanced mixture for people with malnutrition and for the critically or chronically ill, it being possible for the losses induced by catabolic stresses to be compensated and thus treated, or else the deficiency states occurring even at the start of the disorder to be intercepted in the sense of protection before collapse of the intestinal intestinal barrier. In addition, it is ensured that the synergistic effect of the substrates supplied in combination can be utilized and the imbalances otherwise occurring on administration of individual substrates on their own in extremely high dosage, with subsequent metabolic disturbance, can be prevented.

Glutamine is a nonessential amino acid for healthy people and plays a central part as intermediate in nitrogen metabolism. Glutamine acts as nitrogen donor in the synthesis of purines, pyrimidines, nucleotides, aminosaccharides and glutathione and represents the principal substrate for the formation of ammonia in the kidney (regulation of the acid/base equilibrium). Glutamine further acts as nitrogen transport substance between numerous tissues. Finally, glutamine is the principal energy supplier for the metabolism of the cells of the gastrointestinal tract (enterocytes, colonocytes) and for rapidly proliferating cells such as those of the immune system.

In the critically ill, e.g. patients after an elective operation, after major traumas, burns, infections or else within the framework of pancreatitis, the elevated catabolic and metabolic states are associated—irrespective of the nutritional status just prevailing—with a significant reduction in the glutamine concentration in muscle cells. In addition, peripheral glutamine stores are reduced more quickly during a catabolic stress situation or in tumor-bearing hosts, with the amino acid as energy source being preferentially transported to the intestine or the tumors. The increased rate of reduction then leads to a depletion of glutamine there, resulting in glutamine then being lacking for the enterocytes and immunocytes. It has therefore been proposed to consider glutamine as a provisionally essential amino acid during catabolic stress situations such as a trauma or a sepsis (cf. EP-A-238,553).

It is therefore advantageous in the treatment of stress and malnourished patients to undertake an additional luminal (enteral) nutrition of the intestine with glutamine in order to improve the function of the intestinal barrier and the immune status. The concentration of glutamine should in this case be in the range 15-70 g, preferably from 20 to 50 g, in particular 20 to 45 g, per daily dose. If the supplement solution is prepared shortly before its intended administration, glutamine can be added in free form or as di- or tripeptide with Ala and/or Gly. If, on the other hand, storage of the complete supplement solution and/or sterilization of the complete supplement solution is intended, glutamine should preferably be employed in the form of the dipeptide with Ala or Gly. In this case, the stated amount is based on the proportion of glutamine by weight in the particular dipeptide.

It is known that people with malnutrition or the critically or chronically ill are exposed to increased oxidative stress such as is to be observed for example to be particularly pronounced after ischaemia/reperfusion damage. In such cases there is deregulation of enzyme systems, resulting in an increased occurrence of toxic oxygen free radicals. For defense against oxidative stress, the body maintains under normal conditions a reservoir of various reduced compounds (=antioxidants) such as, for example, ascorbic acid, carotenoids, dihydrolipoic acid. However, trace elements such as selenium and zinc may also act as antioxidants. These endogenous antioxidants do not, however, suffice during malnutrition and during chronic disorders or after an intensive stress event, to which the critically ill may be exposed, to trap the high concentration of free radicals formed or prevent their production. The effect of this is that the pathological manifestation of a systemic inflammation is increased even further during a generalized inflammation. The provision of an appropriate supply of antioxidants is therefore indicated when it is intended to counteract the effect of free radicals and the oxidative damage resulting therefrom.

It is additionally known that antioxidants are mutually dependent in a synergistic manner in relation to their regeneration during the elimination of the free radicals in the body through forming an antioxidant spiral. Thus, for example, vitamin C, vitamin E, glutathione and NADP are oxidized and recover their activity after reduction thereof. Such an antioxidant spiral has also been demonstrated for the interaction of the vitamins C and E, selenium and zinc.

Because of this mutually complementary antioxidant effect of different substrates, it is therefore worthwhile to add at least two of the antioxidahts mentioned hereinafter, but preferably several, especially, however, vitamins C and E, β-carotene and the trace elements selenium and zinc in combination with one another to the supplement of the invention in addition to the two other essential substrates (glutamine and short-chain fatty acids or precursors thereof).

Examples of antioxidants are vitamins having antioxidant properties such as vitamin C or vitamin E; amino acids or amino acid derivatives having antioxidant properties such as S-adenosylmethionine, cysteine, cystine or glutathione; amino sulfonic acids such as taurine; trace elements having antioxidant properties such as selenium or zinc; polyphenols and carotenoids, preferably β-carotene.

The vitamin C requirement in people with malnutrition and the chronically or critically ill is greater than in healthy people. Thus, it has been observed that the ascorbic acid concentration in the plasma of intensive-care patients was distinctly below the normal level of healthy people, despite administration of more than 200 mg of vitamin C per day. In animals with burns it is possible by early administrations of large amounts of ascorbic acid to reduce the amounts of fluid necessary for emergency therapy. Since vitamin C is also involved in the synthesis of collagen, high doses of ascorbic acid are all the more advantageous when required for wound healing in such pathological states. The high vitamin C doses in the enteral supplement I and II can therefore be regarded as suitable compensation for the vitamin C deficiency manifestations otherwise occurring in people with malnutrition and the chronically or critically ill. The amount of vitamin C which may therefore be present in the enteral supplement of the invention is in the range from 0.5 to 4 g, preferably from 1 to 2.5 g, per daily dose.

The lipid-soluble vitamin E (tocopherol) protects proteins, nucleic acids and, in particular, unsaturated fatty acids incorporated into membranes from oxidation by oxygen free radicals. The critically or chronically ill show very low vitamin E levels. The essential cause of secondary damage after injuries to the human skull caused by trauma is suspected to be damage due to free radicals. It was possible to show experimentally that early additions of α-tocopherol, or of α-tocopherol in combination with ascorbic acid, are able to reduce the content of lipid peroxidation products in the brain, thus having a protective effect against the spread of cell damage. The enteral supplement of the invention may therefore have a vitamin E content of from 0.2 to 2 g, preferably from 0.3 to 1.2 g, per daily dose.

There is much evidence in the literature that carotenoids, and of these especially β-carotene, apart from its known ability to trap excited states of triplet and singlet oxygen, are also able to trap peroxyl free radicals and other forms of active oxygen. These properties are particularly significant in cases of reperfusion damage. It is to be assumed that patients with ischaemia/reperfusion damage of tissues produce considerable amounts of singlet oxygen, and β-carotene then represents the specific means for neutralizing this particularly reactive oxygen species. A daily dose of the enteral supplement I or II of the invention may therefore comprise β-carotene in an amount of 5-80 mg, preferably of 10 to 60 mg.

Selenium represents, as a structural component of the active site of glutathione peroxidase, an essential component of the system of intracellular antioxidants. This selenium-dependent enzyme plays the main part in protecting cells from peroxidation damage, especially from lipid peroxidation. Selenium therefore appears to play a direct part in regulating inflammatory processes.

In a systemic inflammatory reaction or sepsis, patients are subject to severe oxidative stress. These patients therefore rapidly show greatly reduced selenium levels, which are associated with increasing renal losses and a reduction in peroxidase activity and the increase in lipid peroxidation products. Some patients with specific pathological conditions are particularly susceptible in this connection: patients with burns, trauma, and haemodialysis patients. It is therefore preferred to provide for the enteral supplement a daily selenium dose of from 0.2 to 1 mg, preferably from 0.2 to 0.6 mg, in order to achieve a normalization of various biological functions in people with malnutrition and the chronically or critically ill.

Zinc represents an essential cofactor for more than 100 enzymes. It has been possible to show that the function of T-helper cells and the activity of natural killer cells is impaired in a zinc deficiency. In addition, impairments both of the antigen-associated and immunoregulatory function of the macrophages and of interleukin-1 release are also to be observed. The injury metabolism of people with malnutrition and the critically or chronically ill is the cause of an increased loss of zinc with the urine. A zinc deficiency may also occur in patients with burns as a result of losses through the skin and in trauma patients as a result of increased diuresis. Addition of 15-40 mg of zinc is proposed, depending on the type of disorder. In order to improve the immune status of the critically ill, therefore a daily zinc dose of from 10 to 60 mg, particularly preferably from 20 to 40 mg, is preferably provided for the enteral supplement I and II of the invention.

The term short-chain fatty acids (SCFA) encompasses specifically acetic acid, propionic acid, butyric acid and pentanoic acid ($C_2$-$C_5$). These can be formed by microbial fermentation of carbohydrates in the gastrointestinal tract of mammals. Butyrate occurs naturally in many fruits and vegetables. The most productive source is butter fat (butter) (3-4% butyrate), where it may occur as ester of glycerol.

Acetate, propionate and butyrate are formed in the virtually constant molar ratio of 60:25:15 by intestinal bacteria and rapidly absorbed by the intestinal mucosa. They are relatively calorie-rich, are metabolized by the intestinal epithelium and the liver and stimulate absorption of water and sodium in the large bowel. They have trophic effects on the intestinal mucosa. In addition, they serve as nutrients and act as genuine essential substrates, because organ function is weakened when they are absent.

Precursors for providing SCFA are bulking agents. The formation of SCFA can thus be effected through a change in the doses of bulking agents. In contrast to this, the butyrate concentration can be significantly reduced by removing bulking agents from the diet. It has additionally been possible to show that butyrate represents the preferred energy substrate for colonocytes. Butyrate also plays a part in preventing certain types of colitis. In the experimental short-bowel syndrome, addition of butyrate to the enteral diet brings about an increased rate of outflow of amino acids from the portal vein, which indicates that butyrate exerts its trophic effect mainly in and via the colon. It has also been possible to show that the butyrate concentration in the plasma can be increased to almost 0.5 mmol after oral administration of glycerol tributyrate in daily doses of from 50 to 400 mg/kg of body weight over a period of 3 weeks, without detectable toxic side effects (cf. B. A. Conley et al., In Clinical Cancer Research, Vol. 4, 629-634, 1998).

It can thus be assumed that short-chain fatty acids such as butyrate may contribute as additional substrate in enteral supplements I and II to an improvement in digestion and absorption in the intestine. These compounds or derivatives thereof, such as tributyrin, are therefore present in the supplement of the invention with a daily dose of from 0.5 to 10 g, preferably from 1 to 6 g. To assist and improve the immune status in people with malnutrition and the critically or chronically ill there is a need for an increased proliferation of immune cells, which depends on an increased DNA and RNA synthesis rate. During the infections following a trauma, therefore, there is an increased requirement for nucleotides in order to cope with the necessary production of immune cells. Synthesis to give the polynucleotide chains of DNA and RNA from the corresponding energy-rich deoxyribonucleoside triphosphates and ribonucleoside triphosphates is catalyzed by the respective DNA and RNA polymerases. The energy-rich deoxyribonucleoside triphosphates and ribonucleoside triphosphates are produced by phosphorylation reactions from the corresponding deoxyribonucleoside monophosphates and ribonucleoside monophosphates (=nucleotides).

Nucleotides thus represent important components for the synthesis of DNA and RNA. Adequate amounts of purines and pyrimidines are necessary for nucleotide synthesis which makes requirements. In healthy people, these are efficiently absorbed from the diet, in which they are normally present in an amount of 1-2 g per day. Purines and pyrimidines are either synthesized denovo or obtained by recovery reactions in nucleotide metabolism (salvage pathway), whereby intermediates of nucleic acid degradation are rescued from total degradation and can be reused for renewed synthesis of nucleic acids. The cell is able to save large amounts of energy in this way.

If protein intake is sufficient, in healthy people the denovo synthesis represents the main source for maintaining nucleotide availability, with glutamine being the main nitrogen donor.

In people with malnutrition and the critically or chronically ill it is possible for the adequate availability of nucleic acids to be impaired, because expression of synthesis enzymes in the denovo synthesis pathway is evidently impaired during catabolic stress, which may lead to the depletion of nucleotides. A decreased availability of nucleotides then results in an impairment of T-cell function, a reduction in the activity of natural killer cells, delayed host reactions, a suppression of the proliferation of lymphocytes and a reduced interleukin-2 production. It has been possible to show that in the critically ill a removal of nucleotides from the diet reduces the phagocytosis ability and compromises the clearance of experimentally introduced pathogens. Most of these effects prove to be reversible through reinclusion of nucleotides in the food supplied.

In a preferred embodiment, therefore, precursors for the synthesis of DNA, RNA and/or energy-rich phosphates are added to the enteral supplement of the invention to support and improve the immune status, in particular in the form of nucleotides, preferably from yeast. A daily dose should preferably be in the range from 1.5 to 15 g, particularly preferably in the range from 2 to 6 g.

Further additions to the enteral supplement of the invention may be ribose, folic acid, B vitamins and lysophosphatidic acid.

Glycine is a nonessential amino acid and is usually present in all solutions for artificial nutrition. Recent investigations have shown that glycine has cytoprotective and anti-inflammatory and antineoplastic properties. It has additionally been possible to show that during hypoxia (reduced $O_2$ partial pressure) glycine maintains the integrity of the cell membranes and thus is able to prevent release of intracellular enzymes. After administration of lipopolysaccharides, glycine is able to inhibit the synthesis and release of proinflammatory cytokines and eicosanoids in the Kupfer cells of the liver by reducing the Ca level in the cytosol.

Because of its Ca-antagonistic effects, which acts advantageously on the immune status as a result of the inhibitory effect on the formation of proinflammatory cytokines and eicosanoids (series 2 and 4), glycine can preferably be added to the supplement of the invention in an amount of 5-70 g, particularly preferably from 10 preferably from 10 to 40 g, based on a daily dose. If glycine is employed together with glutamine as dipeptide, the stated amount is based on the proportion of glycine by weight in the dipeptide.

In a particularly preferred embodiment, the supplement of the invention contains, based on a daily dose: 20-45 g, in particular 30 g, of glutamine, 5-20 g, in particular 10 g, of glycine, 1.5-5 g, in particular 2 g, of nucleotides, 0.5-5 g, in particular 1 g, of tributyrin, 5-50 g of maltodextrins, 2-30 mg, in particular 10 mg, of β-carotene, 200-1000 mg, in particular 500 g, of vitamin E, 500-2000 mg, in particular 1500 g, of vitamin C, 200-600 μg, in particular 300 μg, of selenium and 10-30 mg, in particular 20 mg, of zinc.

It has been known for a long time that chromium is connected with an improvement in glucose tolerance and that the utilizability of glucose is impaired in chromium deficiency. It has been possible to show that the demand for insulin declined in non-insulin-dependent diabetes mellitus, which indicates that chromium was able to increase the effect of insulin.

A strong insulin resistance may occur in people with malnutrition and the critically or chronically ill, so that additional administration of chromium has proved to be an advantageous therapeutic procedure in these patients. It was also possible to show that trivalent chromium is nontoxic. Thus, autopsy of a female patient who received chromium in parenteral form for 21 years revealed no evidence of carcinogenic properties.

It is therefore advantageous to add up to a maximum of 1 mg of chromium to the supplement to be administered enterally in addition to the partial parenteral nutrition.

Further possible ingredients of the supplement of the invention are proteins, of which up to 30 g may be present, based on a daily dose, and/or additional (going beyond the content of short-chain fatty acids or precursors thereof) fats, of which up to up to 45 g may be present, based on a daily dose.

Proteins are preferably employed in the form of a protein hydrolyzate.

Additional fats may be medium chain and/or long-chain fatty acids which may be saturated and/or unsaturated. It is also possible to employ derivatives of these fatty acids, such as salts, esters, especially glycerol esters or phospholipids, or amides. Medium chain fatty acids have 6-12 carbon atoms. Long-chain fatty acids have 13 to 22 carbon atoms.

Lipids are able to undertake tasks which go far beyond their function as energy suppliers or as cellular structural components. Lipids are to be regarded as pharmacological active substances which are provided by nutrition. This applies in particular to the polyunsaturated fatty acids (PUFAs).

Enteral intake of increased amounts of n-3 polyunsaturated fatty acids (n-3 PUFAa), like those to be found for example in fish oil as eicosapentaenoic acid (EPA) and docosahexaenoic acid (DHA), is associated with a change in the ratio of n-3 to n-6 PUFAs in the phospholipid spectrum in favor of the n-3 PUFAs. This has an influence on the immune function, with essentially two effects applying, which may moreover be subject to mutual influencing:

1. a change in membrane fluidity and
2. a change in the release of membrane-bound lipids produced by hydrolysis from membrane-associated phospholipids.

Re 1) changes in the fluidity may influence the receptor binder of cytokines and other agonists. The state of the membrane fluidity moreover has an influence on intracellular signal transmission, which may affect, for example, the activity of G proteins and subsequently lead to changes in activity of enzyme systems (adenylate kinase, phospholipase $A_2$, phospholipase C). In addition, polyunsaturated fatty acids are important precursors for the formation of so-called second messengers such as diacylglycerol and ceramides. Administration of fish oil is therefore associated with profound changes in intracellular signal transduction, which may influence the production and release of cytokines, interleukins and interferons.

Re 2) under the influence of the enzyme phospholipase $A_2$, PUFAs can be released from membrane phospholipids. After their hydrolysis, they are used as precursors to form lipid mediators. Polyunsaturated fatty acids are converted into eicosanoids in the cyclooxygenase and lipoxygenase pathways. The principal advantages of the eicosanoids derived from n-3 PUFAs can be summarized by comparison with the eicosanoids derived from n-6 PUFAs as follows:

1. thromboxane $A_3$ ($TxA_3$), which is derived from eicosapentaenoic acid (EPA) in the cyclooxygenase pathway, has a less aggregating and thus prothrombotic effect on platelets than $TxA_2$, which is derived from n-6 PUFAs.
2. EPA is converted in the lipoxygenase pathway into $LTB_5$ which has a considerably lower activity than $LTB_4$ (from n-6 PUFAs) and therefore induces a markedly reduced chemotactically induced migration and less endothelial adherence of immunocompetent cells.
3. $PGE_2$, which is derived from n-3 PUFAs, has a markedly smaller immunosuppressant effect than $PGE_2$, which is derived from n-6 PUFAs.

Via these mechanisms of action, n-3 PUFAs influence the immune response which is impaired during a trauma or an infection in two ways:

1. there is a reduction in the frequently existing hyperinflammation.
2. under the conditions of stress metabolism there is an enhancement of the immunological defense functions.

Re 1) it has been possible to show that it was possible to diminish hyperinflammatory processes by increased administration of n-3 fatty acids compared with n-6 fatty acids. In particular, EPA reduced the release of cytokines having proinflammatory activity, such as IL-1, IL-6 and TNF-α and -β. In addition, administration of fish oil leads to a reduced release of proinflammatory substances such as leukotriene $B_4$ and PAF, and to reduced local formation of thromboxane $A_2$. It was possible to demonstrate in particular by the example of Crohn's disease and ulcerative colitis that existing signs of inflammation can be alleviated through supplying fish oil in the diet.

Re 2) in the critically ill there is evidence of an augmented influence of n-3 PUFAs on the cellular defense function, which connects the reduction in prostaglandins of series 2 (e.g. $PGE_2$) with a reduced feedback inhibition and, associated therewith, a "booster effect" on the cellular defense function. This idea is supported by findings which show that administration of n-3 PUFAs during SIRS or sepsis increase cytokine production, optimize antigen presentation, enhance splenocyte proliferation, improve the opsonization ability and reduce the mortality.

The advantages of enteral administration of n-3 PUFAs can be summarized as follows:

1. reduction in the inflammatory immune response.
2. restoration of the defense function of immunocompetent cells through reducing the stress-induced $PGE_2$ release.
3. antiarrhythmic properties.
4. antithrombotic properties.
5. maintenance of the microcirculation.

For this reason, the fat content (maximum 45 g of fat) in supplement II consists, besides medium-chain triglycerides (MCT), preferably of fish oil, which is known to be rich in the n-3 fatty acids EPA and DHA. The n-3 fatty acids are in this case present in the triglyceride system. It is then possible and preferred for supplement II to have a content of n-3 fatty acids in the range from 5 to 15 g, particularly preferably in the range from 6 to 10 g, based on a daily dose. (A) fish oil(s) should preferably be employed either alone or mixed in such a ratio to one another that the ratio of n-3 fatty acids to n-6 fatty acids is about 1:1.

In a very particularly preferred embodiment, the supplement of the invention contains, based on a daily dose: 20-45 g, in particular 30 g, of glutamine, 5-20 g, in particular 10 g, of glycine, 1.5-5 g, in particular 2 g, of nucleotides, 0.5-5 g, in particular 1 g, of tributyrin, 5-100 g, in particular 90 g, of maltodextrins, 2-30 mg, in particular 10 mg, of β-carotene, 200-1000 mg, in particular 500 mg, of vitamin E, 500-2000 mg, in particular 1500 mg, of vitamin C, 200-600 μg, in particular 300 μg, of selenium, 10-30 mg, in particular 20 mg, of zinc, 200-600 μg, in particular 400 μg, of chromium, 15-30 g, in particular 20 g, of protein hydrolyzate, a total of 15-30 g, in particular 22 g, of additional fats, of which 7-12 g, in particular 10 g, are medium-chain fatty acids and 4-8 g, in particular 6 g, are n-3 fatty acids from fish oil with an n-3/n-6 ratio of >=1:1, further vitamins, trace elements and minerals.

The invention is explained in more detail by means of the following examples.

EXAMPLE 1

Corresponding to Supplement I

A liquid supplement to be administered enterally to a person with malnutrition or critically or chronically ill patient in addition to a parenteral complete food or in addition to enteral/oral nutrition for the start of treatment had, based on a daily dose, the following composition:

| Volume: 500 ml | |
|---|---|
| Glutamine | 30 g |
| Glycine | 10 g |
| Maltodextrins | 16 g |
| Tributyrin | 1 g |
| Nucleotides | 2 g |
| Antioxidants: | |
| β-Carotene | 10 mg |
| Vitamin C | 1500 mg |
| Vitamin E | 500 mg |
| Selenium | 300 μg |
| Zinc | 20 mg |

The supplement comprised about 250 kcal and had a caloric density of about 0.5 kcal/ml, an osmolality of 500 mosmol/kg of water and an osmolarity of 455 mosmol/liter of water.

EXAMPLE 2

Corresponding to Supplement II

A liquid supplement to be administered enterally to a person with malnutrition or critically or chronically ill patient in addition to a partial parenteral nutrition or in addition to enteral/oral nutrition had, based on a daily dose, the following composition:

| Volume: 1000 ml | |
|---|---|
| Protein hydrolyzate (from whey) | 20 g |
| Glutamine | 30 g |
| Glycine | 10 g |
| Maltodextrins | 90 g |
| Tributyrin | 1 g |
| Nucleotides | 2 g |

-continued

| Antioxidants: | |
|---|---|
| β-Carotene | 10 mg |
| Vitamin C | 1500 mg |
| Vitamin E | 500 mg |
| Selenium | 300 μg |
| Zinc | 20 mg |
| Fats: | 22 g |
| n-3 fatty acids (from fish oil) | 6 g |
| n-3/n-6 ratio | 1/1 |
| Chromium | 400 μg |

The supplement comprised about 800 kcal and had a caloric density of about 0.8 kcal/ml, an osmolality of 530 mosmol/kg of water and an osmolarity of 425 mosmol/liter of water. The protein:carbohydrates:fat ratio as percentages by weight was approximately 30:45:25. Supplement II additionally comprises further vitamins and trace elements, and minerals in amounts which correlated with the energy content.

EXAMPLE 3

This Example Describes the Influence of Administering the Composition of the Invention on the Plasma Level of Surgical Patients 1500 ml of the composition described below were administered to surgical patients continuously by means of a feeding pump each day for 10 days starting with the first postoperative day.

The daily dose of the composition comprised 30 g of glutamine, 10 g of glycine, 224 g of maltodextrins, 1 g of tributyrin, 10 mg of β-carotene, 1500 mg of vitamin C, 500 mg of vitamin E, 300 μg of selenium, 20 mg of zinc, 68 g of whey protein hydrolyzate and 65 g of fats, of which 6 g were n-3 fatty acids from fish oil.

Blood samples were taken from the patients before the operation, on the first day after the operation (before starting the supplementation with the test solution) and on the fifth and eleventh day after the operation. The content of selected substrates in the plasma was then determined.

The following table shows the profile of the measured plasma levels of glutamine, zinc, selenium, β-carotene, vitamin C and α-tocopherol on the day before the operation and on the first, fifth and eleventh day after the operation (pre-OP, POD1, POD5 and POD11, respectively).

TABLE

| Plasma constituent | Glutamine (μmol/l) | Zinc (μmol/l) | Selenium (μg/l) | β-Carotene (μmol/l) | Vitamin C (μmol/l) | α-Tocopherol (μmol/l) |
|---|---|---|---|---|---|---|
| Pre-OP (n = 14)*) | 599 ± 121 | 8.44 ± 2.29 | 60.4 ± 18.6 | 0.16 ± 0.11 | 15.08 ± 12.34 | 15.50 ± 3.99 |
| POD1 (n = 14)*) | 508 ± 165 | 4.38 ± 1.57 | 46.0 ± 20.1 | 0.12 ± 0.08 | 10.06 ± 8.54 | 11.08 ± 2.76 |
| POD5 (n = 13)*) | 600 ± 102 | 7.01 ± 1.98 | 69.5 ± 17.2 | 0.22 ± 0.11 | 34.75 ± 19.47 | 29.86 ± 10.64 |
| POD11 (n = 9)*) | 597 ± 83 | 9.20 ± 3.16 | 104.2 ± 35.8 | 0.47 ± 0.22 | 34.51 ± 13.37 | 40.20 ± 14.94 |

*) Number of patients investigated

The results show that in all cases at least a normalization of the plasma levels was achieved and, for some key substrates, it was in fact possible to find a marked increase or improvement compared with the initial situation. The results further show that the key substrates are taken up by people in the intestine and thus contribute to improving the antioxidant status of the patients.

The invention claimed is:

1. A method of using a supplement comprising the step of administering the supplement to a patient enterally for treatment of malnutrition or major abdominal surgery, for the treatment of patients who must be fasted before diagnostic procedures or before surgical interventions, for the treatment of inflammatory bowel disorders, mucositis, stomatitis, short-bowel syndrome or acute pancreatitis, wherein the supplement comprises, as solution, in each case based on a daily dose:
   a) glutamine and/or glutamine precursor selected from the group consisting of glutamine esters, glutamine amides, N-alkylated glutamines, glutamine salts, keto precursors of glutamine and short-chain, glutamine-containing peptides, in a first amount in the range from 15 to 70 g, where in the case of glutamine precursors said first amount is based on the glutamine content thereof,
   b) at least two representatives from the group of substances having antioxidant activity selected from the group consisting of vitamins, amino acids, amino acid derivatives amino sulfonic acid trace elements, polyphenols and carotenoids and
   c) short-chain fatty acids having two to five carbon atoms and/or salts or esters as precursors of short-chain fatty acids having two to five carbon atoms, in a second amount of from 0.5 to 10 g, where in the case of precursors of short-chain fatty acids said second amount is based on the short-chain fatty acid content thereof and wherein said daily dose is 200 to 1000 ml, and the supplement has a total energy content of no more than 1000 kcal/200 ml.

2. The method of claim 1, wherein said supplement is in sterilized and liquid form ready for use.

3. The method of claim 1, wherein said glutamine and/or glutamine precursors are present in the range of from 20-45 g, calculated as glutamine, based on a daily dose.

4. The method of claim 1, wherein the glutamine precursors are in the form of short-chain, glutamine-containing dipeptides.

5. A method of (i) maintaining or restoring the intestinal barrier of a critically or chronically ill patient or a patient with malnutrition or (ii) treating a critically or chronically ill patient or a patient with malnutrition, comprising enterally administering to said patient a daily dose of 200 ml to 1,000 ml of a supplement to maintain or restore the intestinal barrier of said patient, wherein the supplement comprises, as solution, in each case based on a daily dose:
   a) glutamine and/or glutamine precursor selected from the group consisting of glutamine esters, glutamine amides, N-alkylated glutamines, glutamine salts, keto precursors of glutamine and short-chain, glutamine-containing peptides, in a first amount in the range from 15 to 70 g, where in the case of glutamine precursors said first amount is based on the glutamine content thereof, b) at least two representatives from the group of substances having antioxidant activity selected from the group consisting of vitamins, amino acids, amino acid derivatives, amino sulfonic acid, trace elements, polyphenols and carotenoids, and c) short-chain fatty acids having two to five carbon atoms and/or salts or esters as precursors of short-chain fatty acids having two to five carbon atoms, in a second amount of from 0.5 to 10 g, where in the case of precursors of short-chain fatty acids said second amount is based on the short-chain fatty acid content thereof and wherein said daily dose is 200 to 1000 ml, and the supplement has a total energy content of no more than 1000 kcal/200 ml.

6. The method of claim 5, wherein the daily dose of said supplement is 500 ml.

7. The method of claim 5, wherein the method further comprises providing to said patient a partial or complete parenteral nutrition.

8. The method of claim 5, wherein said supplement is in sterilized and liquid form ready for use.

9. The method of claim 5, wherein said glutamine and/or glutamine precursors are present in the range of from 20-45 g, calculated as glutamine, based on a daily dose.

10. The method of claim 5, wherein the glutamine precursors are in the form of short-chain, glutamine-containing dipeptides.

11. The method of claim 5, wherein said precursors of shortchain fatty acids are present in the form of glycerol esters of short-chain fatty acids.

12. The method of claim 11, wherein said glycerol esters of shortchain fatty acids comprise tributyrin.

13. The method of claim 5, wherein the antioxidants are selected from the group consisting of vitamin C, vitamin E, S-adenosyl-methionine, cysteine, cystine, glutathione, taurine, selenium, zinc, polyphenols and carotenoids.

14. The method of claim 13, wherein the carotenoids comprise β-carotene.

15. The method of claim 11, wherein said antioxidants are selected from the group consisting of vitamin C with a content in the range from 0.5 to 4 g, vitamin E with a content in the range from 0.2 to 2 g, β-carotene with a content in the range from 5 to 80 mg, selenium with a content in the range from 0.2 to 1 mg, and zinc with a content in the range from 10 to 60 mg, in each case based on a daily dose.

16. The method of claim 5, wherein said antioxidants are vitamin C, vitamin E, β-carotene, selenium and zinc in combination.

17. The method of claim 15, wherein the amount of selenium is from 0.3 to 0.6 mg.

18. The method of claim 5, wherein said supplement additionally comprises precursors for the synthesis of DNA, RNA and/or energy-rich phosphates.

19. The method of claim 18, wherein the precursors are nucleotides which correspond to the DNA, RNA and/or energy-rich phosphates.

20. The method of claim 19, wherein said nucleotides are present in the range from 1.5 to 15 g, based on a daily dose.

21. The method of claim 5, wherein said supplement additionally comprises one or more substances from the group of ribose, folic acid, B vitamins and lysophosphatidic acid.

22. The method of claim 5, wherein said supplement additionally comprises at least one substance having a Ca-antagonistic effect.

23. The method of claim 22, wherein said substance having a Ca-antagonistic effect is glycine.

24. The method of claim 23, wherein said glycine is present in the range from 5 to 70 g, based on a daily dose.

25. The method of claim 5, wherein said supplement comprises, based on a daily dose: 20-45 g of glutamine, 5-20 g of glycine, 1.5-5 g of nucleotides, 0.5-5 g of tributyrin, 5-50 g of maltodextrins, 2-30 mg of β-carotene, 200-1000 mg of vitamin E, 500-2500 mg of vitamin C, 200-600 μg of selenium and 10-30 mg of zinc.

26. The method of claim 5, wherein said supplement additionally comprises, based on a daily dose, at least one component selected from the group consisting of up to 30 g of proteins, up to 45 g of fats and up to 1 mg chromium.

27. The method of claim 26, wherein said proteins are present in the form of a protein hydrolyzate.

28. The method of claim 26, wherein the additional fats comprise medium-chain fatty acids.

29. The method of claim 26, wherein the additional fats comprise a high content of n-3 fatty acids.

30. The method of claim 29, wherein the n-3 fatty acids comprise eicosapentaenoic acid and/or docosahexaenoic acid.

31. The method of claim 29, wherein the fat comprises a fish oil or a mixture of different fish oils.

32. The method of claim 26, wherein the supplement comprises, based on a daily dose: 20-45 g of glutamine, 5-20 g of glycine, 1.5-5 g of nucleotides, 0.5-5 g of tributyrin, 5-100 g of maltodextrins, 2-30 mg of β-carotene, 200-1000 mg of vitamin E, 500-2000 mg of vitamin C, 200-600 μg of selenium, 10-30 mg of zinc, 200-600 μg of chromium, 15-30 g of protein hydrolyzate, and a total of 15-30 g of additional fats, of which 7-12 g are medium-chain fatty acids and 4-8 g are n-3 fatty acids from fish oil with an n-3/n-6 ratio of greater than or equal to 1:1.

33. The method of claim 5, wherein said supplement has a total energy content per daily dose of up to 400 kcal and a daily dose of up to 500 ml.

* * * * *